US00PP14501P39

(12) United States Plant Patent
Pieters

(10) Patent No.: US PP14,501 P3
(45) Date of Patent: Feb. 3, 2004

(54) CHRYSANTHEMUM PLANT NAMED 'GEDI TWO PAD'

(50) Latin Name: *Chrysanthemum morifolium*
Varietal Denomination: Gedi Two Pad

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 10/138,115

(22) Filed: May 1, 2002

(65) Prior Publication Data

US 2003/0208818 P1 Nov. 6, 2003

(51) Int. Cl.[7] ..... A01H 5/00
(52) U.S. Cl. ..... Plt./292
(58) Field of Search ..... Plt./292, 291, 287, Plt./286

(56) References Cited

U.S. PATENT DOCUMENTS

PP11,300 P 3/2000 Boeder ..... Plt./287

OTHER PUBLICATIONS

Brummitt, Horticultural Science Chrysanthemum once again, The Garden, 1997, pp. 662–663.*

* cited by examiner

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar is disclosed, characterized by a decorative-type inflorescence with disc florets becoming more visible with aging, consistent flowering response to short days, blooming consistently after 63 days of short day length, free branching habit, purple ray florets, a very uniform round growth habit, and a large quantity of blooms per flowering branch.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Gedi Two Pad.'

BACKGROUND OF THE INVENTION

The new cultivar is a product of hybridization of a female parent variety, 'Cassano' (undistributed in the United States) and a male parent variety 'Ampiro' (undistributed in the United States). The new cultivar was discovered and selected by the inventor in September 1996.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Gedi Two Pad' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Pad.' These characteristics in combination distinguish 'Gedi Two Pad' as a new and distinct Chrysanthemum cultivar:

1. Decorative-type inflorescence with disc florets becoming more visible with aging,
2. Consistent flowering response to short days, blooming consistently after 63 days of short day length, 3. Free branching habit,
4. Purple ray florets,
5. Very uniform round growth habit, and
6. Large quantity of blooms per flowering branch.

Plants of the new cultivar are similar to plants of the female parent variety, 'Cassano' in most horticultural characteristics, however plants of the new cultivar have fewer disc florets and plants of the new cultivar bloom naturally three weeks earlier than plants of the female parent variety.

Plants of the new cultivar are similar to plants of the male parent variety, 'Ampiro,' however the new cultivar a wider diameter inflorescence and naturally blooms three weeks earlier than plants of the male parent variety.

In comparison to the commercially available variety 'Cleargar' (U.S. Plant Pat. No. 11,300), 'Gedi Two Pad' blooms earlier naturally, has more inflorescences per flowering branch, and has fewer ray florets.

BRIEF DESCRIPTION OF THE PHOTOGRAPH

The photograph shows a plant of 'Gedi Two Pad' grown in a six-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in Oxnard, Calif. during the month of December and January. The age of the observed plants is 86 days from a rooted cutting. The growing temperature ranged from 55° to 68° F. at night to 60° to 75° F. during the day.

Measurements and numerical values represent averages of typical flowering types.

Botanical classification: *Chrysanthemum morifolium* cultivar 'Gedi Two Pad'.
Commercial classification: Garden-type Chrysanthemum.
Parentage: Hybridization of a female parent variety, 'Cassano' (undistributed in the United States), and a male parent variety 'Ampiro' (undistributed in the United States).

PROPAGATION

Time to rooting: 7 to 14 days at approximately 21° C.
Root description: Fine, fibrous.

PLANT

Growth habit: Mounding herbaceous perennial.
Height: Approximately 32 cm.
Spread: Approximately 33 cm.
Growth rate: Moderate.
Branching characteristics: Free branching.
Length of lateral branches: Approximately 28.8 cm.
Number of leaves per lateral branch: Approximately 15.

FOLIAGE

Leaf:
- *Arrangement.*—Alternate.
- *Average length.*—Approximately 5.8 cm.
- *Average width.*—Approximately 4.3 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near 137A. Young foliage under side: Near 138A. Mature foliage upper side: Near 137A. Mature foliage under side: Near 138A. Venation upper side: Near 144B. Venation under side: Near 138B.
- *Venation type.*—Palmately net.

Petiole:
- *Average length.*—Approximately 2.2 cm.
- *Color.*—Near 137A.
- *Diameter.*—Approximately 0.2 cm.

BLOOM

Inflorescence:
- *Flowering habit.*—Induced by darkness period greater than 13.5 hours, approximately 63 days of appropriate day length required to induce and develop blooms.
- *Inflorescence form.*—Decorative.
- *Natural flowering season.*—Approximately the last week of August through the first week of September.
- *Number of inflorescences per lateral branch.*—Approximately 21.
- *Inflorescence diameter.*—Approximately 4.1 cm.
- *Inflorescence depth.*—Approximately 1.5 cm.
- *Inflorescence longevity on plant.*—Approximately 15 days.
- *Persistence.*—Persistent.
- *Changes as inflorescence ages.*—Disc florets become more visible.

Ray florets:
- *Appearance.*—Matte.
- *Texture.*—Smooth.
- *Average number per flower.*—123.
- *Shape.*—Oblong.
- *Aspect.*—Flat.
- *Margin.*—Entire.
- *Apex.*—Retuse.
- *Length.*—Approximately 2.1 cm.
- *Width.*—Approximately 0.7 cm.
- *Color.*—Upper surface at first opening: Near 64B. Upper surface at maturity: Near 64D. Upper surface at fading: Near 63D. Under surface at first opening: Near 64B. Under surface at maturity: Near59D. Under surface at fading: Near 64D.

Disc florets:
- *Diameter of disc.*—Approximately 0.5 cm (becomes apparent only at fading).
- *Appearance.*—Shiny.
- *Texture.*—Smooth.
- *Average number per flower.*—Approximately 13.
- *Shape.*—Cylindric.
- *Apex.*—Obtuse.
- *Average length.*—Approximately 0.5 cm.
- *Average width.*—Approximately 0.1 cm.
- *Color.*—At first opening: Near 154B. At maturity: Near 14A. At fading: Near 13A.

Peduncle:
- *Length.*—At terminal end (shortest): Approximately 3.1 cm. At lateral end (longest): Approximately 7.4 cm.
- *Angle to stem.*—Acute.
- *Strength.*—Moderate.
- *Color.*—Near 138B.
- *Habit.*—Upright.
- *Diameter.*—Approximately 0.2 cm.
- *Surface texture.*—Lightly pubescent.

Inflorescence bud:
- *Length.*—Approximately 0.9 cm.
- *Diameter.*—Approximately 0.9 cm.
- *Form.*—Globular.
- *Color* (*as ray florets are just emerging*).—Near 77A.

Involucral bracts (phyllaries):
- *Appearance.*—Matte.
- *Texture.*—Lightly pubescent.
- *Number.*—Approximately 21.
- *Shape.*—Oblanceolate.
- *Margin.*—Entire.
- *Apex.*—Acute.
- *Length.*—Approximately 0.9 cm.
- *Width.*—Approximately 0.4 cm.
- *Color.*—Upper side: Near 137B. Under side: Near 138A.

REPRODUCTIVE ORGANS

Ray florets:
- *Number of pistils per flower.*—1.
- *Stigma shape.*—2 branched.
- *Stigma color.*—Near 3A.
- *Style color.*—Near 154C.
- *Style length.*—Approximately 0.5 cm.
- *Stamens.*—Absent.

Disc florets:
- *Number of pistils per flower.*—1.
- *Stigma shape.*—Two-branched.
- *Stigma color.*—Near 6A.
- *Style length.*—Approximately 0.4 cm.

*Style color.*—Near 154D.
*Number of stamens per flower.*—4.
*Anther shape.*—Tubular.
*Anther color.*—Near 13A.
*Pollen.*—No pollen detected.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests has been observed in this cultivar.

Heat and cold resistance: Plants with flowers are hardy to low temperatures about −2° C. Non flowering plants are hardy in the approximate range of 3° C. to −6° C., depending upon duration of cold and amount of moisture in the soil. With adequate water plants are hardy to a high temperature of 49° C.

What is claimed is:

1. A new and distinct cultivar of Chrysanthemum plant named 'Gedi Two Pad' as herein illustrated and described.

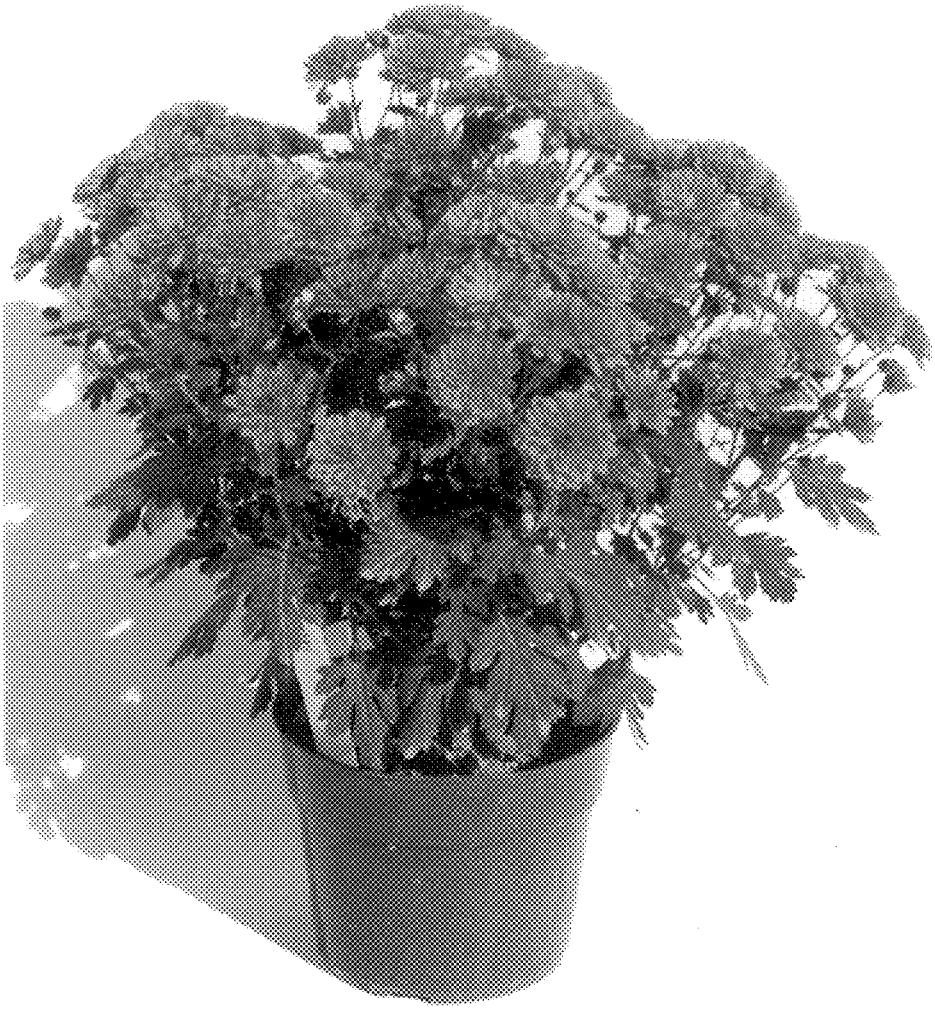

* * * * *